US00PP30792P2

(12) United States Plant Patent
Pellett

(10) Patent No.: US PP30,792 P2
(45) Date of Patent: Aug. 13, 2019

(54) ***PHYSOCARPUS* PLANT NAMED 'UMNHARPELL'**

(50) Latin Name: *Physocarpus opulifolius*
Varietal Denomination: UMNHarpell

(71) Applicant: REGENTS OF THE UNIVERSITY OF MINNESOTA, Minneapolis, MN (US)

(72) Inventor: Harold M. Pellett

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

(21) Appl. No.: 15/732,958

(22) Filed: Jan. 16, 2018

(51) Int. Cl.
*A01H 5/12* (2018.01)

(52) U.S. Cl.
USPC ..... Plt./226
CPC ..... *A01H 5/12* (2013.01)

(58) Field of Classification Search
USPC ..... Plt./226
See application file for complete search history.

*Primary Examiner* — Anne Marie Grunberg
(74) *Attorney, Agent, or Firm* — Penny J. Aguirre

(57) ABSTRACT

A new cultivar of *Physocarpus* plant, 'UMNHarpell', that is characterized by its new foliage that is red-purple in color and matures to deep purple with the deep purple color retained into the interior of the plant, its compact plant habit, its slow to moderate growth rate, and its good resistance to powdery mildew.

2 Drawing Sheets

Genus/species: *Physocarpus opulifolius.*
Varietal denomination: 'UMNHarpell'.

BACKGROUND OF THE INVENTION

The present invention relates to a new and distinct cultivar of *Physocarpus opulifolius* and will be referred to hereafter by its cultivar name, 'UMNHarpell'. 'UMNHarpell' represents a new cultivar of *Physocarpus*, a deciduous shrub grown for landscape use.

The new *Physocarpus* arose from a breeding program conducted by the Inventor in Donald, Oreg. The objective of the breeding program was to develop new *Physocarpus* cultivars with unique foliage color combined with compact plant habits.

The new *Physocarpus* originated from open pollination in spring of 2002 of *Physocarpus* 'Center Glow' (U.S. Plant Pat. No. 16,894) and proprietary seedlings that were previously derived from crosses between *Physocarpus* cultivars 'Monlo' (U.S. Plant Pat. No. 11,211) and 'Dart's Gold' (not patented). The seeds were pooled and the new cultivar 'UMNHarpell' was selected as a unique single plant from the resulting seedlings in spring of 2003.

Asexual reproduction of the new cultivar was first accomplished by softwood cuttings in summer of 2004 in Donald, Oreg. under the direction of the Inventor. The characteristics of this cultivar have been determined to be stable and are reproduced true to type in successive generations.

SUMMARY OF THE INVENTION

The following traits have been repeatedly observed and represent the characteristics of the new *Physocarpus*. These attributes in combination distinguish 'UMNHarpell' as unique and distinct cultivar of *Physocarpus*.

1. 'UMNHarpell' exhibits new foliage that is red-purple in color and matures to deep purple with the deep purple color retained into the interior of the plant.

2. 'UMNHarpell' exhibits a compact plant habit.
3. 'UMNHarpell' exhibits a slow to moderate growth rate.
4. 'UMNHarpell' exhibits good resistance to powdery mildew.

'UMNHarpell' is most closely compared to *Physocarpus opulifolius* cultivars 'Center Glow', 'Monlo', and 'Seward' (U.S. Plant Pat. No. 14,821). 'Center Glow' differs from 'UMNHarpell' in having new foliage that is coppery orange in color, a more vigorous growth habit, a larger plant size, and in having poor resistance to powdery mildew. 'Monlo' is similar to 'UMNHarpell' in having deep purple older foliage. 'Monlo' differs from 'UMNHarpell' in having larger leaves, a more vigorous growth habit, purple foliage that fades in the interior of the plant to bronze green, and lower leaf surfaces that are green in color. 'Seward' is similar to 'UMNHarpell' in having leaves that are similar in size and purple in color. 'Seward' differs from 'UMNHarpell' in having purple foliage that fades in the interior of the plant to bronze green, new foliage that is bronze purple in color, lower leaf surfaces that have red-purple veins, and in having a more vigorous growth habit.

BRIEF DESCRIPTION OF THE DRAWINGS

The accompanying photographs were taken of a five year-old plant of 'UMNHarpell' as grown outdoors in a trial bed in Cottage Grove, Minn.

The photograph in FIG. 1 was provides a view of the plant habit of 'UMNHarpell'.

Figure 1:
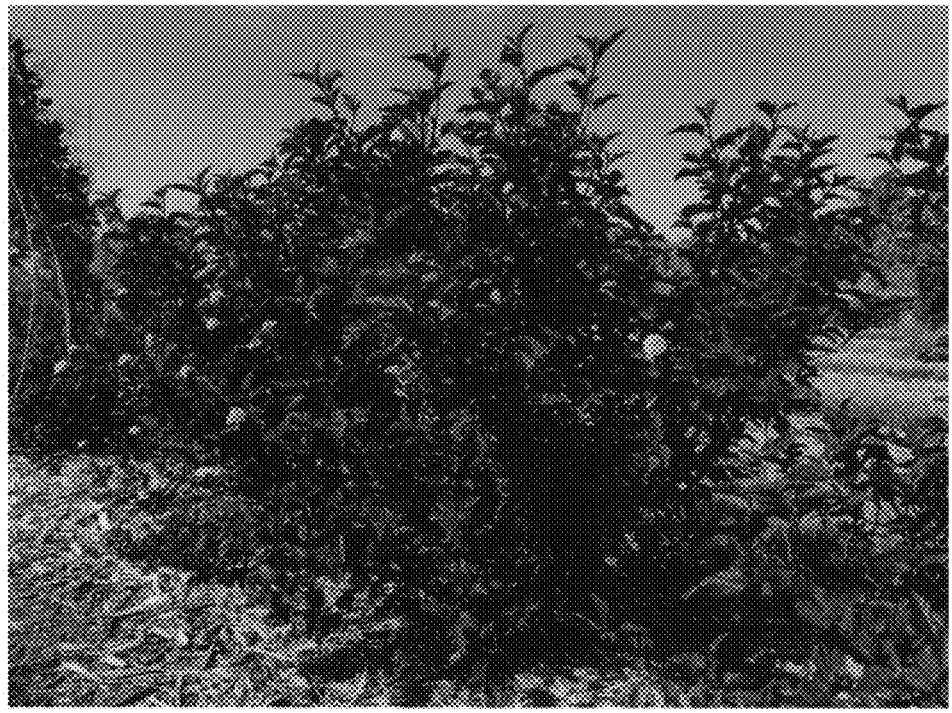
Figure 2:
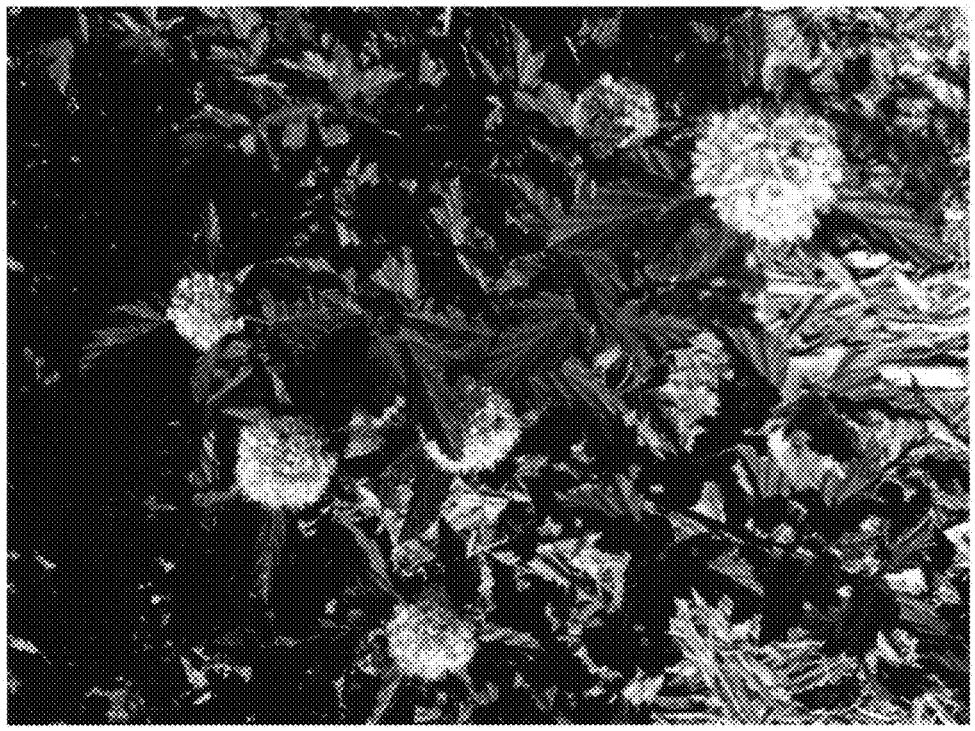

The photograph in FIG. 2 provides a close-up view of the inflorescence and new and mature foliage of 'UMNHarpell'.

The colors in the photographs are as close as possible with the digital photography and printing techniques utilized and the color codes in the detailed botanical description more accurately describe the colors of the new *Physocarpus.*

BOTANICAL DESCRIPTION OF THE PLANT

The following is a detailed description of five year-old plants of the new cultivar as grown in a trial bed in Cottage Grove, Minn. The phenotype of the new cultivar may vary with variations in environmental, climatic, and cultural conditions, as it has not been tested under all possible environmental conditions. The color determination is in accordance with The 2015 R.H.S. Colour Chart of The Royal Horticultural Society, London, England, except where general color terms of ordinary dictionary significance are used.

General description:

*Blooming period.*—2 weeks in early June in Minnesota.

*Plant habit.*—Deciduous shrub.

*Plant habit.*—Densely foliated and compact.

*Height and spread.*—An average of 80 cm in height and 70 cm in spread as a five year-old plant and reaches 1.5 to 2.1 m in height and 1.2 to 1.8 m in spread as a mature plant in the landscape.

*Cold hardiness.*—At least in U.S.D.A. Zone 3.

*Diseases.*—Good disease resistance has been observed to powdery mildew caused by *Podosphaera aphanis* var. *physocarpi.*

*Growth rate.*—Slow to moderate.

*Root development.*—Roots initiate in about 30 days and will fully root as a young plant in a 2-inch plug in about 75 days in summer.

Branch description:

*Branch color.*—Young stems; between 183A and 185A, mature bark; a range of 200B, N200A, where the bark is pealing it is between 161A and 155D, old twigs; ranging between 177B and N199B.

*Branch shape.*—Rounded to quadrangular.

*Branch size.*—Maine branches; up to 80 cm in length, 2 cm in diameter, lateral branches; up to 35 cm in length, 5 mm in diameter, tertiary branches; average of 8 cm in length and 2 mm in diameter.

*Branch surface.*—New growth; glossy and very sparsely pubescent, mature bark; smooth, slightly peeling and matte to shiny, old twigs; glabrous and dull.

*Branching.*—Medium to densely branched, main branches; an average of 11, strong, lateral branches; an average of 26, strong, tertiary branches; an average of 9 per lateral branch, moderately strong.

Foliage description:

*Leaf shape.*—Cordate to narrow.

*Leaf division.*—Simple.

*Leaf base.*—Cuneate to slightly cordate.

*Leaf apex.*—Acute.

*Leaf venation.*—Palmate, upper surface; 161A, lower surface; 161B and sometimes flushed with 184A.

*Leaf margin.*—3-lobed with lobes crenate.

*Leaf attachment.*—Petiolate.

*Leaf arrangement.*—Alternate.

*Leaf surface.*—Upper surface is glossy at the base and matte at the tips and towards the center, lower surface is matte, both surfaces are crinkly.

*Leaf size.*—An average of 6 cm in length and 3.5 cm in width.

*Leaf number.*—Average of 60 per lateral branch 30 cm in length.

*Internode length.*—An average of 2 cm.

*Leaf color.*—Young leaves upper surface; very base N144A, blending up and turning 166A, tips are 200B, young leaves lower surface; a blend of 146A and 174A, mature leaves upper surface; 200A, mature leaves lower surface; a blend of N200A and 200A.

*Petioles.*—1.5 cm in length, 2 cm in diameter, matches stem color, medium strength, glossy and very sparsely pubescent surface.

*Stipules.*—2 at the base of each leaf, 1 cm in length, 2 mm in width, matches leaf color, both surfaces matte, acute apex, attached base is cuneate in shape and crenate margins.

Flower description:

*Flower type.*—Small rotate flowers arranged in spherical corymb, similar to parents and typical of the species *Physocarpus opulifolius.*

*Flower fragrance.*—Very lightly sweet.

*Flower lastingness.*—Corymb lasts about 2 weeks, not persistent, individual flowers about 3 days.

*Flower bud description.*—Elliptic to round in shape, average of 4 cm in length and 3 mm in diameter, a blend of 63A and 62D in color.

*Flower quantity.*—About 58 flowers per corymb.

*Inflorescence size.*—Average of 3 cm in depth and diameter.

*Flower size.*—About 5 mm in depth, 1 cm in diameter.

*Peduncles.*—Average of 1 cm in length and 3 mm in diameter, 199A with a flush of 58A and 83A, glabrous surface.

*Pedicels.*—Average of 7 mm in length and 1 mm in diameter, 161D with a flush of 58A, glabrous surface.

*Petal description.*—5, broadly obtuse in shape, margin is entire, lower and upper surface is glabrous, apex is obtuse, base is obtuse.

*Petal size.*—About 4 mm in length, 3 mm in width.

*Petal color.*—When opening and fully open upper and lower surface; a blend of 155B and 51C and 51A.

*Calyx size.*—Average of 3 mm in diameter, glabrous surface, inner surface color is 25A, outer surface color is mostly 20A with a light flush of 38A.

*Sepal description.*—5, subulate in shape, margin is entire, apex is acute, surface is glabrous, an average of 3 cm in length and 2 mm in width, a blend of 1A and 39A and 38B in color.

Reproductive organs:

*Gynoecium.*—Pistil; 4, average of 4 mm in length, stigma; 0.5 mm in diameter, round and flattened in shape and 18A in color, style; 3.5 mm in length and 18A in color, ovary; 4, oblong in shape, 1 mm in length, 0.5 mm in diameter, superior, 18A in color.

*Androecium.*—Stamens; an average of 29, 5 mm in length, anthers; oblong to rounded in shape, 0.5 mm in diameter, 187A in color, filaments; 4.5 mm in length, NN155D in color, pollen not observed.

*Fruit and seed.*—Fruit a firm-walled inflated follicle, splitting open at both seams, ovoid in shape, seeds; 2 to 4 seeds are hard, shiny, ovoid in shape, N199 in color at maturity.

It is claimed:

1. A new and distinct cultivar of *Physocarpus* plant named 'UMNHarpell' substantially as herein illustrated and described.

* * * * *